US009279007B2

(12) United States Patent
Do

(10) Patent No.: US 9,279,007 B2
(45) Date of Patent: Mar. 8, 2016

(54) SIGNAL SEQUENCES TO IMPROVE PROTEIN EXPRESSIONS AND SECRETION OF RECOMBINANT ENZYMES AND OTHER PROTEINS

(75) Inventor: Hung Do, New Hope, PA (US)

(73) Assignee: Amicus Therapeutics, Inc., Cranbury, NJ (US)

( * ) Notice: Subject to any disclaimer, the term of this patent is extended or adjusted under 35 U.S.C. 154(b) by 0 days.

(21) Appl. No.: 13/988,946

(22) PCT Filed: Nov. 22, 2011

(86) PCT No.: PCT/US2011/061862
§ 371 (c)(1), (2), (4) Date: Aug. 7, 2013

(87) PCT Pub. No.: WO2012/071422
PCT Pub. Date: May 31, 2012

(65) Prior Publication Data
US 2014/0045216 A1    Feb. 13, 2014

Related U.S. Application Data

(60) Provisional application No. 61/415,926, filed on Nov. 22, 2010.

(51) Int. Cl.
| C07K 14/47 | (2006.01) |
| C12N 9/00 | (2006.01) |
| C12N 9/24 | (2006.01) |
| C12N 9/42 | (2006.01) |
| C12N 15/85 | (2006.01) |

(52) U.S. Cl.
CPC .............. *C07K 14/47* (2013.01); *C12N 9/0002* (2013.01); *C12N 9/2402* (2013.01); *C12N 9/2434* (2013.01); *C12N 15/85* (2013.01); *C07K 2319/036* (2013.01)

(58) Field of Classification Search
CPC ..................... C07K 2319/02; C07K 2319/036; C12N 15/85
See application file for complete search history.

(56) References Cited

PUBLICATIONS

Hochstrasser, Ubiquitin-dependent protein degradation., Annu. Rev. Genet. (1996), vol. 30, p. 405-439.*
Guo et al., Protein tolerance to random amino acid change, 2004, Proc. Natl. Acad. Sci. USA 101: 9205-9210.*
Lazar et al., Transforming Growth Factor α: Mutation of Aspartic Acid 47 and Leucine 48 Results in Different Biological Activity, 1988, Mol. Cell. Biol. 8:1247-1252.*

(Continued)

*Primary Examiner* — Alexander Kim
(74) *Attorney, Agent, or Firm* — Servilla Whitney LLC

(57) ABSTRACT

Polypeptide signal sequences of modified fragments of human immunoglobulin heavy chain binding protein (Bip) are disclosed. Also disclosed are fusion proteins comprising a modified fragment of human immunoglobulin heavy chain binding protein (Bip) operably linked to a heterologous polypeptide. Also disclosed are protein expression vectors comprising a promoter operably linked to a first DNA sequence encoding a signal sequence comprising a modified fragment of human immunoglobulin heavy chain binding protein (Bip) and a second DNA sequence encoding a heterologous polypeptide fused in frame to the first DNA sequence. Further disclosed are methods of producing a polypeptide comprising expressing a fusion protein comprising a polypeptide signal sequences of modified fragments of human immunoglobulin heavy chain binding protein (Bip) operably linked to a heterologous polypeptide and recovering the heterologous polypeptide.

18 Claims, 3 Drawing Sheets

Differential Expression and Secretion of Acid β-Glucocerebrosidase

(56) References Cited

PUBLICATIONS

Hill et al., Functional Analysis of conserved Histidines in ADP-Glucose Pyrophosphorylase from *Escherichia coli*, 1998, Biochem. Biophys. Res. Comm. 244:573-577.*

Wacey et al., Disentangling the perturbational effects of amino acid substitutions in the DNA-binding domain of p53., Hum Genet, 1999, vol. 104, pp. 15-22.*

Martoglio et al., Signal sequences: more than just greasy peptides., Trends in Cell biology (1998), vol. 8, Issue 10, Oct. 1, 1998, pp. 410-415.*

Kilian et al., Identification and characterization of a new conserved motif within the presequence of proteins targeted into complex diatom plastids., The Plant Journal (2005), vol. 41, pp. 175-183.*

CFP UniProtKB (last viewed on Jul. 10, 2015).*

PCT International Search Report and Written Opinion in PCT/US2011/061862, dated May 30, 2012, 9 pages.

Deng, Wu-Guo et al., Aspirin and salicylate bind to immunoglobulin heavy chain binding protein (BiP) and inhibit its ATPase activity in human fibroblasts, *FASEB J.*, vol. 15, No. 13, Nov. 2001, 2463-2470.

Wu, Chia-Kuei et al., Targeting to the endoplasmic reticulum improves the folding of recombinant human telomerase reverse transcriptase, *Protein Expr. Purif.*, vol. 56, No. 1, Nov. 2007, 8-19 (http://www.ncbi.nlm.nih.gov/pmc/articles/PMC2790190/pdf/nihms32968.pdf).

Extended European Search Report in EP11843849.8, dated Nov. 26, 2014, 6 pages.

Ciplys, Evaldas, et al., Generation of human ER chaperone BiP in yeast *Saccharomyces cerevisiae*, *Microbial Cell Factories* vol. 12 No. 22 2014, 9 pages.

Freiden, Pamela J., et al., Interconversion of three differentially modified and assembled forms of BiP, *The EMBO Journal* vol. 11 No. 1 1992, 63-70.

Ming-Chi, Lu, et al., Anti-Citrullinated Protein Antibodies Bing Surface-Expressed Citrullinated Grp78 on Monocyte/Macrophages and Stimulate Tumor Necrosis Factor α Production, *Arthritis & Rheumatism*, vol. 62 No. 5 May 2010, 1213-1223.

Wu, Juan-Juan, "Molecular Chaperon and MHC", *International Journal of Immunology*, Issue 6, vol. 27 Nov. 2004, 358-361.

Analysis of the role of the gene bipA, encoding the major endoplasmic reticulum chaperone protein in the secretion of homologous and heterologous proteins in black Aspergilli, *Applied Mircobiology and Biotechnology* vol. 50 1998, 447-454.

RecName: Full=78 kDa glucose-regulated protein, UniProt:Q354T7, Oct. 3, 2006, 2 pages.

* cited by examiner

```
                        SEQUENCE LISTING

<160> NUMBER OF SEQ ID NOS: 24

<210> SEQ ID NO 1
<211> LENGTH: 44
<212> TYPE: DNA
<213> ORGANISM: Artificial Sequence
<220> FEATURE:
<223> OTHER INFORMATION: Synthetic primer

<400> SEQUENCE: 1
ggcaagatct gaattcggga tggagttttc aagtccttcc agag              44

<210> SEQ ID NO 2
<211> LENGTH: 45
<212> TYPE: DNA
<213> ORGANISM: Artificial Sequence
<220> FEATURE:
<223> OTHER INFORMATION: Synthetic primer

<400> SEQUENCE: 2
tcgagcggcc gcaagctagc ttatcactgg cgacgccaca ggtag             45
```

<210> SEQ ID NO 3
<211> LENGTH: 34
<212> TYPE: DNA
<213> ORGANISM: Artificial Sequence
<220> FEATURE:
<223> OTHER INFORMATION: Synthetic primer

<400> SEQUENCE: 3
ccacgaattc caagatgaag ctctccctgg tggc                          34

<210> SEQ ID NO 4
<211> LENGTH: 31
<212> TYPE: DNA
<213> ORGANISM: Artificial Sequence
<220> FEATURE:
<223> OTHER INFORMATION: Synthetic primer

<400> SEQUENCE: 4
ctggccatgg gtacccggat gatgttatat c                             31

<210> SEQ ID NO 5
<211> LENGTH: 30
<212> TYPE: DNA
<213> ORGANISM: Artificial Sequence
<220> FEATURE:
<223> OTHER INFORMATION: Synthetic primer

<400> SEQUENCE: 5
ccacgaattc gacaatgcag ctgaggaacc                               30

<210> SEQ ID NO 6
<211> LENGTH: 44
<212> TYPE: DNA
<213> ORGANISM: Artificial Sequence
<220> FEATURE:
<223> OTHER INFORMATION: Synthetic primer

<400> SEQUENCE: 6
ctcgaagcgg ccgcttaaag taagtctttt aatgacatct gcat               44

<210> SEQ ID NO 7
<211> LENGTH: 19
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: Phosphorylated primer

<400> SEQUENCE: 7
gcactggaca atggattgg                                           19

<210> SEQ ID NO 8
<211> LENGTH: 27
<212> TYPE: DNA
<213> ORGANISM: Artificial Sequence
<220> FEATURE:
<223> OTHER INFORMATION: Synthetic primer

<400> SEQUENCE: 8
ccacgaattc aaccatggga gtgaggc                                  27

<210> SEQ ID NO 9
<211> LENGTH: 36
<212> TYPE: DNA

```
<213> ORGANISM: Artificial Sequence
<220> FEATURE:
<223> OTHER INFORMATION: Synthetic primer

<400> SEQUENCE: 9
ctcgaagcgg ccgcctaaca ccagctgacg agaaac                                36

<210> SEQ ID NO 10
<211> LENGTH: 15
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: Phosphorylated primer

<400> SEQUENCE: 10
gctgcactcc tgggg                                                       15

<210> SEQ ID NO 11
<211> LENGTH: 18
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: Phosphorylated primer

<400> SEQUENCE: 11
gctcagcagg gagccagc                                                    18

<210> SEQ ID NO 12
<211> LENGTH: 17
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: Phosphorylated primer

<400> SEQUENCE: 12
gcagtgccca cacagtg                                                     17

<210> SEQ ID NO 13
<211> LENGTH: 441
<212> TYPE: DNA
<213> ORGANISM: Homo sapiens
<220> FEATURE:
<221> NAME/KEY: misc_feature
<223> OTHER INFORMATION: Minigene 1 (native human Bip-GlcCerase)

<400> SEQUENCE: 13
acggaattcg aaacgatgaa gctctccctg gtggccgcga tgctgctgct gctcagcgcg      60
gcgcgggccg cccgccccctg catccctaaa agcttcggct acagctcggt ggtgtgtgtc    120
tgcaatgcca catactgtga ctccttttgac ccccgacct ttcctgccct tggtaccttc     180
agccgctatg agagtacacg cagtgggcga cggatggagc tgagtatggg gcccatccag    240
gctaatcaca cgggcacagg cctgctactg accctgcagc cagaacagaa gttccagaaa    300
gtgaagggat ttggagggggc catgacagat gctgctgctc tcaacatcct tgccctgtca    360
ccccctgccc aaaatttgct acttaaatcg tacttctctg aagaaggaat cggatataac    420
atcatccggg tacccatggc c                                              441
```

<210> SEQ ID NO 14
<211> LENGTH: 471
<212> TYPE: DNA
<213> ORGANISM: Artificial Sequence
<220> FEATURE:
<223> OTHER INFORMATION: Minigene 2 (modified Bip signal
      sequence-1-GlcCerase)

<400> SEQUENCE: 14

```
acggaattcg aaacgatgaa gctctccctg gtggccgcga tgctgctgct gctcagcctg      60
gtggccgcga tgctgctgct gctcagcgcg gcgcgggccg cccgccctg catccctaaa     120 agcttcggct acagctcggt ggtgtgtgtc tgcaatgcca catactgtga ctcctttgac    180
cccccgacct ttcctgccct tggtaccttc agccgctatg agagtacacg cagtgggcga    240
cggatggagc tgagtatggg gcccatccag gctaatcaca cggcacagg cctgctactg     300 accctgcagc cagaacagaa gttccagaaa gtgaagggat ttggaggggc catgacagat    360
gctgctgctc tcaacatcct tgccctgtca ccccctgccc aaaatttgct acttaaatcg    420
tacttctctg aagaaggaat cggatataac atcatccggg tacccatggc c             471
```

<210> SEQ ID NO 15
<211> LENGTH: 106
<212> TYPE: DNA
<213> ORGANISM: Artificial Sequence
<220> FEATURE:
<223> OTHER INFORMATION: Minigene 3 (Modified Bip signal sequence-1)

<400> SEQUENCE: 15

```
acggaattcg caagatgaag ctctccctgg tggccgcgat gctgctgctg ctcagcctgg     60
tggccgcgat gctgctgctg ctcagcgcgg cgaggcctgc ggccgc                   106
```

<210> SEQ ID NO 16
<211> LENGTH: 102
<212> TYPE: DNA
<213> ORGANISM: Artificial Sequence
<220> FEATURE:
<223> OTHER INFORMATION: Minegene 4 (Modified Bip signal sequence-2)

<400> SEQUENCE: 16

```
ggtaccgaat cgctggcaa gatgaagctc tccctggtgg ccgcgatgct gctgctgctc      60
tgggtggcac tgctgctgct cagcgcggcg aggccttcta ga                       102
```

<210> SEQ ID NO 17
<211> LENGTH: 105
<212> TYPE: DNA
<213> ORGANISM: Artificial Sequence
<220> FEATURE:
<223> OTHER INFORMATION: Minegene 5 (Modified Bip signal sequence-3)

<400> SEQUENCE: 17

```
ggtaccgaat cgctggcaa gatgaagctc tccctggtgg ccgcgatgct gctgctgctc      60
tccctggtgg ccctgctgct gctcagcgcg gcgaggcctt ctaga                    105
```

<210> SEQ ID NO 18
<211> LENGTH: 105
<212> TYPE: DNA
<213> ORGANISM: Artificial Sequence
<220> FEATURE:
<223> OTHER INFORMATION: Minegene 6 (Modified Bip signal sequence-4)

<400> SEQUENCE: 18

```
ggtaccgaat cgctggcaa gatgaagctc tccctggtgg ccgcgatgct gctgctgctc    60
gcactggtgg ccctgctgct gctcagcgcg gcgaggcctt ctaga                 105
```

<210> SEQ ID NO 19
<211> LENGTH: 18
<212> TYPE: PRT
<213> ORGANISM: Homo sapiens
<220> FEATURE:
<221> NAME/KEY: misc_feature
<223> OTHER INFORMATION: Native human Bip signal sequence

<400> SEQUENCE: 19

```
Met Lys Leu Ser Leu Val Ala Ala Met Leu Leu Leu Leu Ser Ala Ala
1               5                   10                  15

Arg Ala
```

<210> SEQ ID NO 20
<211> LENGTH: 28
<212> TYPE: PRT
<213> ORGANISM: Artificial Sequence
<220> FEATURE:
<223> OTHER INFORMATION: Modified Bip ss-1

<400> SEQUENCE: 20

```
Met Lys Leu Ser Leu Val Ala Ala Met Leu Leu Leu Leu Ser Leu Val
1               5                   10                  15

Ala Ala Met Leu Leu Leu Leu Ser Ala Ala Arg Ala
            20                  25
```

<210> SEQ ID NO 21
<211> LENGTH: 25
<212> TYPE: PRT
<213> ORGANISM: Artificial Sequence
<220> FEATURE:
<223> OTHER INFORMATION: Modified Bip ss-2

<400> SEQUENCE: 21

```
Met Lys Leu Ser Leu Val Ala Ala Met Leu Leu Leu Leu Trp Val Ala
1               5                   10                  15

Leu Leu Leu Leu Ser Ala Ala Arg Ala
            20                  25
```

<210> SEQ ID NO 22
<211> LENGTH: 26
<212> TYPE: PRT
<213> ORGANISM: Artificial Sequence
<220> FEATURE:
<223> OTHER INFORMATION: Modified Bip ss-3

<400> SEQUENCE: 22

```
Met Lys Leu Ser Leu Val Ala Ala Met Leu Leu Leu Leu Ser Leu Val
1               5                   10                  15

Ala Leu Leu Leu Leu Ser Ala Ala Arg Ala
            20                  25
```

<210> SEQ ID NO 23
<211> LENGTH: 27
<212> TYPE: PRT
<213> ORGANISM: Artificial Sequence
<220> FEATURE:
<223> OTHER INFORMATION: Modified Bip ss-4

<400> SEQUENCE: 23

```
Met Lys Leu Ser Leu Val Ala Ala Met Leu Leu Leu Ala Leu Val
1               5                   10                  15

Ala Leu Leu Leu Leu Arg Ser Ala Ala Arg Ala
            20                  25

<210> SEQ ID NO 24
<211> LENGTH: 5
<212> TYPE: PRT
<213> ORGANISM: Homo sapiens
<220> FEATURE:
<221> NAME/KEY: misc_feature
<223> OTHER INFORMATION: Signal peptidase recognition sequence for
      native human Bip

<400> SEQUENCE: 24

Ser Ala Ala Arg Ala
1               5
```

SIGNAL SEQUENCES TO IMPROVE PROTEIN EXPRESSIONS AND SECRETION OF RECOMBINANT ENZYMES AND OTHER PROTEINS

CROSS-REFERENCE TO RELATED APPLICATIONS

This application is the National Stage of International Application No. PCT/US2011/061862, filed Nov. 22, 2011, which claims the benefit of U.S. Provisional Application Ser. No. 61/415,926, filed Nov. 22, 2010, the disclosures of which are incorporated herein by reference in their entireties.

TECHNICAL FIELD

The expression and secretion of recombinant enzymes and other proteins for therapeutic and other uses.

BACKGROUND

In eukaryotes, protein synthesis for nearly all proteins begins in the cytoplasm via mega protein complexes called ribosomes. Various proteins complete their synthesis and folding in the cytoplasm and remain there where they function. However, many others are exported out of the cytoplasm and into the endoplasmic reticulum (ER) where they acquire the needed post-translational modifications (e.g., disulfide bonds, glycosylation, etc.) to attain their proper protein structure and biological activity prior to export to their intended cellular locations (e.g., Golgi, peroxisome and lysosomal proteins) or to the cell surface (e.g., receptors, ion channels, etc.) or secreted out of cells (e.g., antibodies, clotting factors, hormones, etc.). Proteins destined for export out of the cytoplasm are distinguished from cytoplasmic proteins by a specialized protein element at the amino (N-) terminus called the signal sequence.

Signal sequences (also called signal peptides) have no consensus amino acid sequence or length but typically comprise the initial 15-40 residues at the N-terminus with 7-20 contiguous hydrophobic amino acid residues which form an α-helical secondary structure that is often flanked by charged residues. Signal sequences are identified in the cytoplasm by a specialized multi-subunit protein:RNA complex called the signal recognition particle (SRP) which directs these nascent proteins to specialized pores within the ER membrane called translocons where these proteins are transported across the ER membrane into the ER lumen—a process known as protein translocation.

Protein translocation occurs concurrently during protein synthesis (i.e., co-translationally) in mammals while in other eukaryotes (e.g., yeast), this process can be either co- or post-translational. Signal sequence-mediated protein translocation is also utilized in bacteria for directing proteins out of the cytoplasm and into the periplasm. In mammals, signal sequences are identified by SRP as they emerge from ribosomes which temporarily pauses protein translation to allow the targeting of the entire SRP-nascent protein-ribosome complex to translocons via the associated SRP receptor. Protein synthesis is resumed after SRP is released and the ribosome-nascent protein complex is properly docked at the translocon.

Most enzyme and other protein therapeutics are produced by recombinant technology that is designed to secrete these recombinant proteins out of cells and into cell culture to simplify downstream purification. These recombinant enzymes and other proteins therefore must utilize signal sequences and this same cellular pathway for secretion. High-level production of these proteins therefore requires signal sequences that can mediate efficient ER targeting and protein translocation across the ER membrane. However, signal sequences are not equivalent for facilitating ER targeting and translocation. The identification of signal sequences by SRP is believed to occur rapidly and efficiently, but the subsequent ER targeting and translocation steps are highly disparate among proteins. Because signal sequences are recognized twice, first by SRP for targeting the nascent protein-ribosome complex to ER and subsequently by translocon proteins (i.e., Sec61 proteins) and other translocon-associated ER proteins to initiate translocation, both are potential sites for regulation. This latter step has been shown to be much more stringent and less efficient and thus, is a major bottleneck in this process. Surprisingly, most signal sequences are intrinsically inefficient for facilitating protein translocation. Consequently, many ER-targeted nascent protein-ribosome complexes dissociate from the ER membrane and protein synthesis is aborted, thereby reducing their protein expression and secretion.

SUMMARY

The present invention provides polypeptide signal sequences, comprising a modified fragment of human immunoglobulin heavy chain binding protein (Bip).

The present invention also provides fusion proteins, comprising a modified fragment of human immunoglobulin heavy chain binding protein (Bip) operably linked to a heterologous polypeptide.

Further provided are protein expression vectors, comprising a promoter operably linked to a first DNA sequence wherein the first DNA sequence encodes a polypeptide signal sequence comprising a modified fragment of human immunoglobulin heavy chain binding protein (Bip) polypeptide signal sequence, and a second DNA sequence which is fused in frame to the first DNA sequence, wherein the second DNA sequence encodes a heterologous polypeptide.

The present invention also provides methods for producing a polypeptide, comprising expressing a fusion protein comprising a polypeptide signal sequence derived from human immunoglobulin heavy chain binding protein (Bip) operably linked to a heterologous polypeptide and recovering said heterologous polypeptide.

Also disclosed are methods of producing a polypeptide, comprising expressing a fusion protein comprising a modified fragment of human immunoglobulin heavy chain binding protein (Bip) polypeptide signal sequence operably linked to a heterologous polypeptide, and recovering said heterologous polypeptide.

The present invention further provides protein expression vectors, comprising a promoter operably linked to a first DNA sequence wherein said first DNA sequence encodes a polypeptide signal sequence comprising a modified fragment of human immunoglobulin heavy chain binding protein (Bip) and a second DNA sequence fused in frame to said first DNA sequence, wherein said second DNA sequence encodes a heterologous polypeptide.

Also disclosed are methods for increasing protein expression, comprising expressing a fusion protein comprising a modified fragment of human immunoglobulin heavy chain binding protein (Bip) and a heterologous protein, and recovering the heterologous protein.

The disclosed invention also provides for methods of increasing protein secretion, comprising expressing a fusion protein comprising a modified fragment of human immunoglobulin heavy chain binding protein (Bip) and a heterologous protein, and recovering the heterologous protein.

BRIEF DESCRIPTION OF THE DRAWINGS

The foregoing and other aspects of the present invention is apparent from the following detailed description of the invention when considered in conjunction with the accompanying drawings. For the purpose of illustrating the invention, there is shown in the drawings embodiments that are presently preferred, it being understood, however, that the invention is not limited to the specific instrumentalities disclosed. The drawings are not necessarily drawn to scale. In the drawings.

DETAILED DESCRIPTION OF ILLUSTRATIVE EMBODIMENTS

Figure 1:
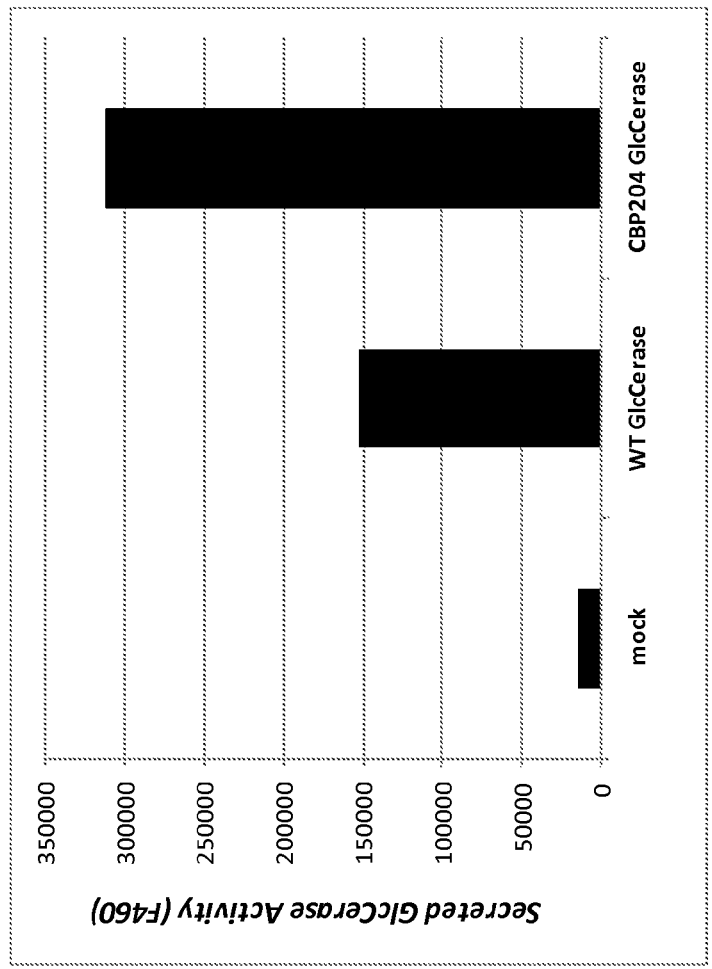
FIG. 1 shows the functional effect of signal sequences for the expression and secretion of recombinant wild-type human acid β-glucocerebrosidase over a period of about 72 hours.

As used herein, a "heterologous polypeptide" is any polypeptide that is not a modified fragment of human immunoglobulin heavy chain binding protein (Bip).

As used herein, "Bip" is an abbreviation for immunoglobulin heavy chain binding protein.

Suitable polypeptide signal sequences can comprise a modified fragment of human immunoglobulin heavy chain binding protein (Bip). The polypeptide signal sequences that comprise a modified fragment of human immunoglobulin heavy chain binding protein (Bip) can comprise the amino acid sequence of SEQ ID NO: 20, SEQ ID NO: 21, SEQ ID NO: 22, or SEQ ID NO: 23.

Suitable fusion proteins can comprise a modified fragment of human immunoglobulin heavy chain binding protein (Bip) operably linked to a heterologous polypeptide. This fusion protein can be characterized as having increased expression in cell culture. The cell culture can also be at non-optimal cell culture conditions. The non-optimal cell culture conditions can be high cell density and depleted nutrients. Other suitable fusion proteins with the modified fragment of human immunoglobulin heavy chain binding protein (Bip) can comprise the amino acid sequence of SEQ ID NO: 20, SEQ ID NO: 21, SEQ ID NO: 22, or SEQ ID NO: 23. All of these fusion proteins can also be characterized as having increased expression in cell culture. The cell culture can also be at non-optimal cell culture conditions. Non-optimal cell culture conditions can be high cell density and depleted nutrients. The heterologous polypeptide can be one or more enzymes, one or more biological response modifiers, one or more toxins, one or more antibodies, one or more fragments of the heterologous polypeptide, or any combination thereof. The heterologous polypeptide can be acid β-glucocerebrosidase. The heterologous polypeptide can also be acid α-galactosidase. The heterologous polypeptide can also be acid α-glucosidase. The heterologous polypeptide can also be proinsulin. The heterologous polypeptide can also be insulin-like growth hormone-2 (IGF-2). The heterologous polypeptide can also be interferon. The heterologous polypeptide can also be a therapeutic antibody. The heterologous polypeptide can also be insulin-like growth hormone-1 (IGF-1).

Other suitable fusion proteins with the modified fragment of human immunoglobulin heavy chain binding protein (Bip) can comprise the amino acid sequence SEQ ID NO: 20, SEQ ID NO: 21, SEQ ID NO: 22, or SEQ ID NO: 23 and the heterologous polypeptide can comprise β-glucocerebrosidase. Those fusion proteins can be characterized as having increased expression in cell culture compared to wild-type β-glucocerebrosidase (β-glucocerebrosidase with the native β-glucocerebrosidase signal sequence). The increased expression in cell culture can be measured by assaying for β-glucocerebrosidase activity over about a 3 day period. The cell culture can also be at non-optimal cell culture conditions. Non-optimal cell culture conditions can be high cell density and depleted nutrients. The increased expression in cell culture with high cell density and depleted nutrients can be measured by assaying for β-glucocerebrosidase activity over about a 3 day period.

Other suitable fusion proteins with the modified fragment of human immunoglobulin heavy chain binding protein (Bip) can comprise the amino acid sequence SEQ ID NO: 20, SEQ ID NO: 21, SEQ ID NO: 22, or SEQ ID NO: 23 and the heterologous polypeptide can comprise acid α-galactosidase. Those fusion proteins can be characterized as having increased expression in cell culture compared to wild-type α-galactosidase (α-galactosidase with the native α-galactosidase signal sequence). The increased expression in cell culture can be measured by assaying for α-galactosidase activity over about a 3 day period. The cell culture can also be at non-optimal cell culture conditions. Non-optimal cell culture conditions can be high cell density and depleted nutrients. The increased expression in cell culture with high cell density and depleted nutrients can be measured by assaying for α-galactosidase activity over about a 3 day period.

Other suitable fusion proteins with the modified fragment of human immunoglobulin heavy chain binding protein (Bip) can comprise the amino acid sequence SEQ ID NO: 20, SEQ ID NO: 21, SEQ ID NO: 22, or SEQ ID NO: 23 and the heterologous polypeptide can comprise acid α-glucosidase. Those fusion proteins can be characterized as having increased expression in cell culture compared to wild-type acid α-glucosidase (acid α-glucosidase with the native acid α-glucosidase signal sequence). The increased expression in cell culture can be measured by assaying for acid α-glucosidase activity over about a 3 day period. The cell culture can also be at non-optimal cell culture conditions. Non-optimal cell culture conditions can be high cell density and depleted nutrients. The increased expression in cell culture with high cell density and depleted nutrients can be measured by assaying for acid α-glucosidase activity over about a 3 day period.

Other suitable fusion proteins with the modified fragment of human immunoglobulin heavy chain binding protein (Bip) can comprise the amino acid sequence SEQ ID NO: 20, SEQ ID NO: 21, SEQ ID NO: 22, or SEQ ID NO: 23 and the heterologous polypeptide can comprise proinsulin. Those fusion proteins can be characterized as having increased expression in cell culture compared to wild-type proinsulin (proinsulin with the native proinsulin signal sequence). The increased expression in cell culture can be measured by assaying for proinsulin activity over about a 3 day period. The cell culture can also be at non-optimal cell culture conditions. Non-optimal cell culture conditions can be high cell density and depleted nutrients. The increased expression in cell culture with high cell density and depleted nutrients can be measured by assaying for proinsulin activity over about a 3 day period.

Other suitable fusion proteins with the modified fragment of human immunoglobulin heavy chain binding protein (Bip) can comprise the amino acid sequence SEQ ID NO: 20, SEQ ID NO: 21, SEQ ID NO: 22, or SEQ ID NO: 23 and the heterologous polypeptide can comprise insulin-like growth hormone-2 (IGF-2). Those fusion proteins can be characterized as having increased expression in cell culture compared to wild-type insulin-like growth hormone-2 (IGF-2) (insulin-like growth hormone-2 (IGF-2) with the native insulin-like growth hormone-2 (IGF-2) signal sequence). The increased expression in cell culture can be measured by assaying for insulin-like growth hormone-2 (IGF-2) activity over about a 3 day period. The cell culture can also be at non-optimal cell culture conditions. Non-optimal cell culture conditions can be high cell density and depleted nutrients. The increased expression in cell culture with high cell density and depleted nutrients can be measured by assaying for insulin-like growth hormone-2 (IGF-2) activity over about a 3 day period.

Other suitable fusion proteins with the modified fragment of human immunoglobulin heavy chain binding protein (Bip) can comprise the amino acid sequence SEQ ID NO: 20, SEQ ID NO: 21, SEQ ID NO: 22, or SEQ ID NO: 23 and the heterologous polypeptide can comprise interferon. Those fusion proteins can be characterized as having increased expression in cell culture compared to wild-type interferon (interferon with the native interferon signal sequence). The increased expression in cell culture can be measured by assaying for interferon activity over about a 3 day period. The cell culture can also be at non-optimal cell culture conditions. Non-optimal cell culture conditions can be high cell density and depleted nutrients. The increased expression in cell culture with high cell density and depleted nutrients can be measured by assaying for interferon activity over about a 3 day period.

Other suitable fusion proteins with the modified fragment of human immunoglobulin heavy chain binding protein (Bip) can comprise the amino acid sequence SEQ ID NO: 20, SEQ ID NO: 21, SEQ ID NO: 22, or SEQ ID NO: 23 and the heterologous polypeptide can comprise a therapeutic antibody. Those fusion proteins can be characterized as having increased expression in cell culture compared to a wild-type therapeutic antibody (a therapeutic antibody with the native therapeutic antibody signal sequence). The increased expression in cell culture can be measured by assaying for a therapeutic antibody activity over about a 3 day period. The cell culture can also be at non-optimal cell culture conditions. Non-optimal cell culture conditions can be high cell density and depleted nutrients. The increased expression in cell culture with high cell density and depleted nutrients can be measured by assaying for therapeutic antibody activity over about a 3 day period.

Other suitable fusion proteins with the modified fragment of human immunoglobulin heavy chain binding protein (Bip) can comprise the amino acid sequence SEQ ID NO: 20, SEQ ID NO: 21, SEQ ID NO: 22, or SEQ ID NO: 23 and the heterologous polypeptide can comprise insulin-like growth hormone-1 (IGF-1). Those fusion proteins can be characterized as having increased expression in cell culture compared to wild-type insulin-like growth hormone-1 (IGF-1) (insulin-like growth hormone-1 (IGF-1) with the native insulin-like growth hormone-1 (IGF-1) signal sequence). The increased expression in cell culture can be measured by assaying for insulin-like growth hormone-1 (IGF-1) activity over about a 3 day period. The cell culture can also be at non-optimal cell culture conditions. Non-optimal cell culture conditions can be high cell density and depleted nutrients. The increased expression in cell culture with high cell density and depleted nutrients can be measured by assaying for insulin-like growth hormone-1 (IGF-1) activity over about a 3 day period.

A suitable protein expression vector can comprise a promoter operably linked to a first DNA sequence encoding a polypeptide signal sequence, comprising a modified fragment of human immunoglobulin heavy chain binding protein (Bip) and a second DNA sequence encoding a heterologous polypeptide, which is fused in frame to the first DNA sequence. The polypeptide signal sequence, comprising a modified fragment of human immunoglobulin heavy chain binding protein (Bip) can comprise the amino acid sequence SEQ ID NO: 20, SEQ ID NO: 21, SEQ ID NO: 22, or SEQ ID NO: 23. The second DNA sequence can encode β-glucocerebrosidase.

A suitable protein expression vector can comprise a promoter operably linked to a first DNA sequence encoding a polypeptide signal sequence, comprising a modified fragment of human immunoglobulin heavy chain binding protein (Bip) and a second DNA sequence encoding a heterologous polypeptide, which is fused in frame to the first DNA sequence. The polypeptide signal sequence, comprising a modified fragment of human immunoglobulin heavy chain binding protein (Bip) can comprise the amino acid sequence SEQ ID NO: 20, SEQ ID NO: 21, SEQ ID NO: 22, or SEQ ID NO: 23. The second DNA sequence can encode acid α-glucosidase.

A suitable protein expression vector can comprise a promoter operably linked to a first DNA sequence encoding a polypeptide signal sequence, comprising a modified fragment of human immunoglobulin heavy chain binding protein (Bip) and a second DNA sequence encoding a heterologous polypeptide, which is fused in frame to the first DNA sequence. The polypeptide signal sequence, comprising a modified fragment of human immunoglobulin heavy chain binding protein (Bip) can comprise the amino acid sequence SEQ ID NO: 20, SEQ ID NO: 21, SEQ ID NO: 22, or SEQ ID NO: 23. The second DNA sequence can encode other heterologous proteins such as acid α-galactosidase. The heterologous polypeptide can also be proinsulin. The heterologous polypeptide can also be insulin-like growth hormone-2 (IGF-2) or insulin-like growth hormone-1 (IGF-1). The heterologous polypeptide can also be interferon. The heterologous polypeptide can also be a therapeutic antibody. The heterologous polypeptide can also be any other protein that is secreted out of cells.

A suitable method of producing a polypeptide can comprise expressing a fusion protein with the modified fragment of human immunoglobulin heavy chain binding protein (Bip) operably linked to a heterologous polypeptide and recovering said heterologous polypeptide. The method for producing a polypeptide can be carried out in cultured cells. The cultured cells can be yeast cells or mammalian cells. The method for producing a polypeptide can be carried out in a transgenic system. That transgenic system can comprise cows, goats, sheep, rabbits, or any combination thereof. Recovery from the transgenic system can be from milk. The transgenic system can also comprise chickens. Recovery from the transgenic system can be from eggs.

A suitable method of making a protein expression vector can comprise linking a promoter operably to a first DNA sequence encoding a polypeptide signal sequence comprising a modified fragment of human immunoglobulin heavy chain binding protein (Bip) and fusing in frame a second DNA sequence encoding a heterologous polypeptide to the first DNA sequence. The method of making a protein expression vector can also have a first DNA sequence that encodes the amino acid sequence SEQ ID NO: 20, SEQ ID NO: 21, SEQ ID NO: 22, or SEQ ID NO: 23. The method of making a protein expression vector can also have a second DNA sequence that encodes acid β-glucocerebrosidase, acid α-galactosidase, acid α-glucosidase, proinsulin, insulin-like growth hormone-2 (IGF-2), interferon, therapeutic antibody or an insulin-like growth hormone-1 (IGF-1) or other proteins that are secreted out of cells.

A suitable method of increasing protein expression can comprise expressing a fusion protein comprising a modified fragment of human immunoglobulin heavy chain binding protein (Bip) and a heterologous protein, and recovering the heterologous protein.

A suitable method of increasing protein secretion can comprise expressing a fusion protein comprising a modified fragment of human immunoglobulin heavy chain binding protein (Bip) and a heterologous protein and recovering the heterologous protein.

EXAMPLE 1

Reagents

Wild-type human β-glucocerebrosidase ("GlcCerase") cDNA (NM_000157.3), wild-type human acid α-galactosidase A (GLA) cDNA (NM_000169.2), wild-type human acid α-glucosidase (GAA) cDNA (NM_000152.2) and wild-type human insulin-like growth factor-2 (IGF-2) cDNA (NM_000612.4) were all purchased from Origene™ (Rockville, Md.) while all oligonucleotide primers and synthetic minigenes were from Integrated DNA Technologies™ (IDT™; Coralville, Iowa). pEF6/V5-HisA mammalian expression vector, Dulbecco's modified Eagle medium (DMEM), fetal bovine serum (FBS) and other tissue culture reagents were obtained from Invitrogen™ (Carlsbad, Calif.). Restriction endonucleases, Phusion-HF DNA Polymerase™, T4 DNA ligase, Antarctic phosphatase, chemically-competent E. coli (DH5α cells) were all purchased from New England Biolabs™ (Ipswich, Mass.). Fluorogenic substrates for various glycosidases were purchased from Research Products International™ (Mt. Prospect, Ill.), DNA Gel Extraction and Miniprep DNA kits were from QIAGEN™ (Valencia, Calif.), PureYield Maxiprep DNA™ kit was from Promega™ (Madison, Wis.). Unless stated otherwise, chemicals were from Sigma™ (St. Louis, Mo.), Fugene-HD™ transfection reagent was from Roche™ (Indianapolis, Ind.), human embryonic kidney cells transformed with the T-antigen (HEK293T) was from ATCC™.

EXAMPLE 2

Plasmid Construction

DNA plasmids were constructed to encode various model proteins containing either their native signal sequences or replaced with modified human Bip signal sequences to evaluate the effect of these signal sequences on the expression and secretion of test proteins.

To evaluate human acid β-glucocerebrosidase (GlcCerase, EC 3.2.1.45), several different DNA plasmids were constructed to encode wild-type GlcCerase with either its native signal sequence or the human Bip signal sequence or a modified Bip signal sequence. To generate wild-type human GlcCerase with its native signal sequence, the entire human GlcCerase cDNA was amplified by PCR via Phusion-HF DNA Polymerase™ using Primers 1 & 2 (Table I) and a GlcCerase cDNA clone (NM_000157.3, Origene). Primer 1 was constructed to contain a 5' Bgl II and an internal EcoRI restriction site that immediately preceded the native GlcCerase Kozak sequence while primer 2 contained 3' NheI and NotI restriction sites that succeeded the stop codon to enable cloning of the PCR product into mammalian expression vectors. The ~1.6 kilobase (kb) PCR product (A) was separated and excised from 1% (w/v) agarose preparative gel and isolated using QIAGEN™'s Gel Extraction Kit™. PCR product A was subsequently digested overnight with restriction endonucleases Bgl II and NotI at 37° C., re-purified and ligated into the pEF6/V5-HisA mammalian expression vector (Invitrogen™) that had been previously digested with BamHI and Not I and dephosphorylated with Antarctic phosphatase using T4 DNA ligase. The Bgl II restriction site was incorporated into primer 1 so that ligation of the Bgl II-digested GlcCerase PCR product into the compatible BamHI site of the pEF6/V5-HisA vector eliminated the BamHI restriction site within the multiple cloning site and this modified expression vector will hereafter be referred to as pEF6'. This DNA construct, designated as pHD101, was used to transform chemically-competent E. coli cells and individual ampicillin-resistant bacterial colonies were expanded and screened by restriction digest reactions using EcoRI & NheI and with BamHI, respectively. A correct plasmid DNA from clone 4 (designated as pHD101.4) was further verified by DNA sequencing and chosen for the expression of wild-type GlcCerase. pHD101.4 was used to construct other plasmids encoding wild-type GlcCerase with either the human Bip signal sequence or modified versions of this Bip signal sequence instead of the native GlcCerase signal sequence. Briefly, a double-stranded DNA minigene (designated as minigene 1 in Table II) was constructed (and synthesized by Integrated DNA Technologies™, IDT™) to contain the native Kozak sequence from the yeast alcohol oxidase 1 (AOX1) gene, the gene for the entire 18-residue native human Bip signal sequence (including its natural signal peptidase recognition sequence: Ser-Ala-Ala-Arg-Ala; SAARA (SEQ ID NO:24)) and the N-terminal 123 amino acid residues of mature wildtype human GlcCerase (nucleotides 118-490). Minigene 1 also contained a 5' EcoRI restriction site which preceded the AOX1 Kozak sequence and a natural NcoI site within the GlcCerase gene at the 3' end to enable cloning into pHD101.4 for replacing the native GlcCerase signal sequence with the human Bip signal sequence. Moreover, this strategy enables construction of DNA plasmids for expression of wild-type GlcCerase (with the Bip signal sequence) in either mammalian or yeast systems (that are under the control of the inducible AOX1 promoter). The design of this and other fusion proteins utilized the SignalP 4.0™ analysis program to predict whether the Bip signal sequence would be cleaved from the test protein.

Additional amino acid residues were added to constructs as needed to facilitate signal sequence cleavage and only sequences that were predicted to have proper signal sequence cleavage were chosen for generating these fusion test proteins. For expression in mammalian systems, the Bip-GlcCerase DNA fragment containing the native human Bip Kozak sequence was synthesized via PCR using Primers 3 &

4 and the minigene 1 DNA template. This ~440 bp PCR product (B) was separated and excised from 1% (w/v) agarose preparative gel and isolated using QIAGEN's Gel Extraction kit. PCR product B was digested overnight with restriction endonucleases EcoRI and Nco I, re-purified and ligated with the NcoI→Not I DNA fragment from pHD101.4 encoding amino acid residues 124-497 of mature wild-type GlcCerase (lacking the native GlcCerase signal sequence) and the ~5.8 kb EcoRI→Not I pEF6' vector DNA fragment as described previously. This DNA construct, designated as pHD201, was checked by restriction digest using EcoRI-Xba I and a correct clone (pHD201.2) was verified by DNA sequencing and subsequently used for evaluating the effects of the human Bip signal sequence on the expression and secretion of wild-type GlcCerase. Similarly, a modified version of the Bip signal sequence (minigene 2) was constructed and synthesized by IDT™ to contain the native Kozak sequence from the AOX1 yeast gene, the first 13 residues of the native human Bip signal sequence followed by a repeat of amino acid residues 4-13, the native Bip signal peptidase recognition sequence (residues 14-18) and the N-terminal 123 residues of mature wild-type human GlcCerase (nucleotides 118-490). This modification of the Bip signal sequence (designated as modified Bip signal sequence-1) expanded the hydrophobic domain so that it spanned the entire ER membrane and lengthened the signal sequence from 18 to 28 residues. For expression in mammalian systems, the modified Bip signal sequence-1-GlcCerase DNA containing the native human Bip Kozak sequence fragment was synthesized via PCR using Primers 3 & 4 and minigene 2 DNA template. This ~470 bp PCR product (C) was isolated from 1% (w/v) agarose preparative gel, digested with EcoRI and Nco I, re-purified and ligated with the Nco I→Not I DNA fragment from pHD101.4 encoding amino acid residues 124-497 of mature wild-type GlcCerase (lacking the native GlcCerase signal sequence) and the ~5.8 kb EcoRI→Not I pEF6' vector DNA fragment as before. This DNA construct, designated as pHD204, was checked by restriction digest using EcoRI and Xba I and a correct clone (pHD204.1) was confirmed by DNA sequencing and subsequently used for evaluating the effects of this modified Bip signal sequence on the expression and secretion of wild-type GlcCerase.

Primers used herein to make DNA constructs are summarized in Table 1.

TABLE 1

| Primer | Strand | Oligonucleotide sequence (5' → 3') | SEQ ID NO: |
|---|---|---|---|
| 1 | (+) | [a] ggca*agatctgaatt*c<u>gggatg</u>gagttttcaagtccttccagag | SEQ ID NO: 1 |
| 2 | (-) | [b] tcgag*cggccgc*aagctag*c*ttatcactggcgacgccacaggtag | SEQ ID NO: 2 |
| 3 | (+) | [c] cca*cgaattc*<u>caagatg</u>aagctctccctggtggc | SEQ ID NO: 3 |
| 4 | (-) | ctgg*ccatggg*tacccggatgatgttatatc | SEQ ID NO: 4 |
| 5 | (+) | cca*cgaattc*gacaatgcagctgaggaacc | SEQ ID NO: 5 |
| 6 | (-) | ctcgaag*cggccgc*ttaaagtaagtcttttaatgacatctgcat | SEQ ID NO: 6 |
| 7 | (-) | [d] P-gcactggacaatggattgg | SEQ ID NO: 7 |
| 8 | (+) | cca*cgaattc*aaccatgggagtgaggc | SEQ ID NO: 8 |
| 9 | (-) | ctcgaag*cggccgc*ctaacaccagctgacgagaaac | SEQ ID NO: 9 |
| 10 | (+) | P-gctgcactcctgggg | SEQ ID NO: 10 |
| 11 | (+) | P-gctcagcagggagccagc | SEQ ID NO: 11 |
| 12 | (+) | P-gcagtgcccacacagtg | SEQ ID NO: 12 |

[a] The ATG start codon is shown in bold text within the native GlcCerase Kozak consensus sequence (underlined). Restriction endonuclease recognition sequences are shown italics.
[b] The stop codon is in bold italics.
[c] The ATG start codon is shown in bold text within the native human Bip Kozak consensus sequence (underlined). Restriction endonuclease recognition sequences are shown in italics.
[d] Phosphorylated primers are designated with 5' "P" symbol.

The modified Bip signal-1 was subsequently appended to other proteins to evaluate its effects on their expression and secretion. Briefly, minigene 3 (Table II) was constructed to contain the first 13 residues of the native human Bip signal sequence followed by a repeat of amino acid residues 4-13 and residues 14-17 of the native Bip signal peptidase recognition sequence. Minigene 3 contained the native Kozak sequence from human Bip as well as a 5' EcoRI and 3' Stu I and Not I restriction sites. Stu I was incorporated into minigene 3 because this restriction enzyme produces a blunt 3' end after AGG (codon for arginine, Arg; R) which serves as the natural Arg at residue 17 from the native Bip signal peptidase cleavage sequence. Therefore, any protein can be ligated to this modified Bip signal sequence fragment provided that an additional alanine is added to the protein sequence at the N-terminus to complete the natural SAARA (SEQ ID NO: 24) signal peptidase recognition sequence.

DNA nucleotide sequences of minigenes for Bip and modified Bip signal sequences are summarized in Table 2.

TABLE 2

```
* Minigene 1 (native human Bip-GlcCerase) SEQ ID NO: 13:
Nucleotide sequence (sense strand, 5' → 3'):
acggaattcgaaacgatgaagctctccctggtggccgcgatgctgctgctgctcagcgcggcgcgggccgcccgcccctgca
tccctaaaagcttcggctacagctcggtggtgtgtgtctgcaatgccacatactgtgactcctttgaccccccgacctttcctgccct
tggtaccttcagccgctatgagagtacacgcagtgggcgacggatggagctgagtatgggcccatccaggctaatcacacgg
gcacaggcctgctactgaccctgcagccagaacagaagttccagaaagtgaagggatttggaggggccatgacagatgctgct
gctctcaacatccttgccctgtcaccccctgcccaaaatttgctacttaaatcgtacttctctgaagaaggaatcggatataacatca
tccgggtacccatggcc Minigene 2 (modified Bip signal sequence-1-GlcCerase) SEQ ID NO: 14:
Nucleotide sequence (sense strand, 5' → 3'):
acggaattcgaaacgatgaagctctccctggtggccgcgatgctgctgctgctcagcctggtggccgcgatgctgctgctgctcagcg
cggcgcgggccgcccgcccctgcatccctaaaagcttcggctacagctcggtggtgtgtgtctgcaatgccacatactgtgact
cctttgaccccccgacctttcctgcccttggtaccttcagccgctatgagagtacacgcagtgggcgacggatggagctgagtat
ggggcccatccaggctaatcacacgggcacaggcctgctactgaccctgcagccagaacagaagttccagaaagtgaaggg
atttggaggggccatgacagatgctgctgctctcaacatccttgccctgtcaccccctgcccaaaatttgctacttaaatcgtacttc
tctgaagaaggaatcggatataacatcatccgggtacccatggcc Minigene 3 (Modified Bip signal sequence-1) SEQ ID NO: 15:
Nucleotide sequence (sense strand, 5' → 3'):
acggaattcgcaagatgaagctctccctggtggccgcgatgctgctgctgctcagcctggtggccgcgatgctgctgctgctca
gcgcggcgaggcctgcggccgc Minegene 4 (Modified Bip signal sequence-2) SEQ ID NO: 16:
Nucleotide sequence (sense strand, 5' → 3'):
ggtaccgaattcgctggcaagatgaagctctccctggtggccgcgatgctgctgctgctctgggtggcactgctgctgctcagc
gcggcgaggccttctaga Minegene 5 (Modified Bip signal sequence-3) SEQ ID NO 17:
Nucleotide sequence (sense strand, 5' → 3'):
ggtaccgaattcgctggcaagatgaagctctccctggtggccgcgatgctgctgctgctctccctggtggccctgctgctgctca
gcgcggcgaggccttctaga Minegene 6 (Modified Bip signal sequence-4) SEQ ID NO 18:
Nucleotide sequence (sense strand, 5' → 3'):
ggtaccgaattcgctggcaagatgaagctctccctggtggccgcgatgctgctgctgctcgcactggtggccctgctgctgctc
agcgcggcgaggccttctaga
```

* The ATG start codon is shown in bold text while the Kozak consensus sequence is underlined.
Restriction endonuclease recognition sequences are shown in italics.

For evaluating acid α-galactosidase A (GLA, EC 3.2.1.22), the wild-type enzyme with its native signal sequence was amplified by PCR using Primers 5 & 6 with the GLA cDNA clone (NM 000169.2, Origene™) template DNA. This ~1.3 kb PCR product was isolated by agarose preparative gel, digested with EcoRI and Not I and ligated to the EcoRI-Not I digested, dephosphorylated pEF6'. This DNA construct was designated as pHD214 and was used for evaluating GLA expression. To construct GLA with the modified Bip signal sequence-1, the mature GLA enzyme was synthesized by PCR using Primers 6 & 7 with the GLA cDNA clone template DNA. This ~1.2 kb PCR product (D) was digested with Not I, isolated from agarose preparative gel and ligated to the EcoRI→Stu I minigene 3 DNA fragment and the EcoRI→Not I-digested pEF6' vector as before. This DNA construct was designated as pHD215 was used for evaluating the effects of this modified Bip signal sequence on the expression and secretion of wild-type GLA.

For evaluating acid α-glucosidase (GAA, EC 3.2.1.0), the entire wild-type GAA enzyme (with its native signal sequence) was amplified by PCR using Primers 8 & 9 with the GAA cDNA clone (NM_000152.2, Origene) template DNA. This ~3 kb PCR product (E) was isolated by agarose preparative gel, digested with EcoRI and Not I and ligated to the EcoRI-Not I digested, dephosphorylated pEF6'. This DNA construct was designated as pHD217 was used for evaluating the expression of GAA with its native signal sequence. Since GAA is expressed with multiple pro-sequences that precede the mature enzyme (Moreland et al., 2005), different GAA proteins with varying lengths were synthesized and appended to the modified Bip signal sequence-1 for testing. A GAA DNA fragment lacking its native signal sequence but containing residues 24-952 was synthesized by PCR using Primers 9 & 10. This ~3 kb PCR product (F) was isolated from agarose preparative gel and digested with Not I and ligated to the EcoRI→Stu I minigene 3 DNA fragment and the EcoRI→Not I-digested pEF6' vector. This DNA construct containing modified Bip signal sequence-1 and GAA (24-952) was designated as pHD218. Similarly, A GAA DNA fragment which lack its native signal sequence but containing residues 57-952 was synthesized by PCR using Primers 9 & 11. This ~2.9 kb PCR product (G) was isolated from agarose preparative gel and ligated to the EcoRI→Stu I minigene 3 DNA fragment and the EcoRI→Not I-digested pEF6' vector as before. This DNA construct containing modified Bip signal sequence-1 and GAA (57-952) was designated as pHD219. A GAA DNA fragment lacking its native signal sequence but containing residues 78-952 was synthesized by PCR using Primers 9 & 12. This ~2.8 kb PCR product (H) was isolated from agarose preparative gel and ligated to the Not I and ligated to the EcoRI→Stu I minigene 3 DNA fragment and the EcoRI→Not I-digested pEF6' vector. This DNA construct containing modified Bip signal sequence-1 and GAA (78-952) was designated as pHD220. The effects of this modified Bip signal sequence-1 as well as the pro-sequences on GAA expression and secretion can therefore be carefully examined using DNA constructs pHD217-220.

Other modified Bip signal sequences (Table III) derived from modified Bip signal sequence-1 were designed and will be evaluated to assess whether these additional modifications can further improve protein expression and secretion. These modifications include replacing serine and leucine residues at positions 14 & 15 with a single tryptophan residue and deleting alanine and methonine residues at positions 18 & 19 within the hydrophobic domain (designated as modified Bip signal sequence-2), deleting alanine and methonine residues at positions 18 & 19 within the hydrophobic domain (designated as modified Bip signal sequence-3) and replacing a serine residue at position 14 with alanine and deleting alanine and methonine residues at positions 18 & 19 within the hydrophobic domain (modified Bip signal sequence-4). These modifications were intended to increase the hydrophobicity of the hydrophobic domain which may further enhance interactions of these signal sequences with key ribosomal and ER translocon proteins and creating a more efficient signal peptidase cleavage site for improving protein translocation and secretion for recombinant proteins.

Other test proteins including human insulin, insulin-like growth factor-2 (IGF-2), antibodies, interferons, apolipoproteins, etc. will also be evaluated to determine whether these modified Bip signal sequences would improve their expression and secretion.

The amino acid sequences for modified Bip signal sequences are summarized in Table 3.

TABLE 3

| Signal sequence ("ss") | Primary amino acid sequence | SEQ ID NO: |
|---|---|---|
| Native human Bip ss | [d] MKLSLVAAMLLLL<u>SAARA</u> | SEQ ID NO: 19 |
| Mod. Bip ss-1 | [e] MKLSLVAAMLLLLSLVAAMLLLL<u>SAARA</u> | SEQ ID NO: 20 |
| Mod. Bip ss-2 | MKLSLVAAMLLLLWVALLLL<u>SAARA</u> | SEQ ID NO: 21 |
| Mod. Bip ss-3 | MKLSLVAAMLLLLSLVALLLL<u>SAARA</u> | SEQ ID NO: 22 |
| Mod. Bip ss-4 | MKLSLVAAMLLLLALVALLLL<u>SAARA</u> | SEQ ID NO: 23 |

[d] The native Bip signal peptidase cleavage sequence (SAARA) (SEQ ID NO: 24) is shown in underlined text.
[e] Specific modifications to the Bip signal sequence are shown in bold text for each modified Bip signal sequence.

EXAMPLE 3

Transient Expression of Test Proteins

For transient expression experiments, HEK293T cells were plated in 12-well tissue culture plates with 1 ml of DMEM medium supplemented with 10% FBS and incubated at 37° C. with a 5% CO2 atmosphere. When the HEK293T cells reached 70-100% confluency, the spent medium was replaced with 1 ml of fresh DMEM/10% FBS medium and each well was transfected with 1 µg plasmid DNA for individual test proteins or PBS (for a mock-transfected negative control) and 3 µl of Fugene™-HD transfection reagent according to the manufacturer's protocol. Transfected cells were incubated for 24-72 hours and checked daily for expression of the individual recombinant enzyme (secreted into medium) via enzyme activity assays and/or by Western blotting and ELISA.

EXAMPLE 4

Enzyme Activity Assays

Recombinant human acid β-glucocerebrosidase (GlcCerase) expression and secretion into cell culture medium was assessed by enzyme activity assays using conditioned medium from transient transfection experiments after 24, 48 or at about 72-hrs and the 4-methylumbelliferyl-β-D-glucopyranoside (4-MU-β-Glc) fluorogenic substrate. Briefly, 20 µl of conditioned media from each sample was harvested at the indicated time points and diluted with 80 µl McIlvane buffer (MI buffer: 50 mM sodium citrate/sodium phosphate (pH 5.2)/0.25% (v/v) Triton X-100/0.25% (w/v) sodium taurocholate) in 0.5 ml microcentrifuge tubes. Twenty five µl of each diluted sample was aliquotted into individual wells of 96-well clear bottom black plates (performed in triplicate) and 50 µl of 6 mM 4-MU-β-Glc substrate (prepared in MI buffer) was added to each well via a multi-channel pipettor. The plates were then sealed with cover tape and incubated at 37° C. for 1 hr. The enzymatic reactions were halted by adding 125 µl of 0.1 M NaOH and the liberated 4-MU fluorescence was read on a fluorescence plate reader using 355 nm excitation and 460 nm emission wavelengths, respectively. The 4-MU fluorescence from the mock-transfected sample served as the "background" control and subtracted from all GlcCerase samples.

Recombinant human acid α-glucosidase (GAA) expression and secretion was measured by enzyme activity assays using conditioned medium from transient transfection experiments after 24, 48 or 72-hrs and the 4-methylumbelliferyl-α-D-glucopyranoside (4-MU-α-Glc) fluorogenic substrate. Specifically, 20 µl of conditioned media from each sample was harvested at the different time points and diluted with 80 µl 50 mM sodium acetate buffer (pH 4.0) in 0.5 ml microcentrifuge tubes. Twenty five µl of each diluted sample was aliquotted into individual wells of 96-well clear bottom black plates (in triplicate) and 50 µl of 6 mM 4-MU-α-Glc substrate (prepared in 50 mM sodium acetate buffer, pH 4.0) was added to each well via a multi-channel pipettor. The plates was then sealed with cover tape and incubated at 37° C. for 1 hr. The enzymatic reactions was halted by adding 125 µl of 0.1 M NaOH and the liberated 4-MU fluorescence was read on a fluorescence plate reader using 355 nm excitation and 460 nm emission wavelengths, respectively. The 4-MU fluorescence from the mock-transfected sample served as the "background" control and subtracted from all GAA samples.

Recombinant human acid α-galactosidase (GLA) expression and secretion will be measured by enzyme activity assays using conditioned medium from transient transfection experiments after 24, 48 or 72-hrs and the 4-methylumbelliferyl-α-D-galactopyranoside (4-MU-α-Gal) fluorogenic substrate. Specifically, 20 µl of conditioned media from each sample will be harvested at the different time points and diluted with 80 µl 50 mM sodium citrate/sodium phosphate buffer (pH 4.6) in 0.5 ml microcentrifuge tubes. Twenty five µl of each diluted sample will be aliquotted into individual wells of 96-well clear bottom black plates (in triplicate) and 50 µl of 8 mM 4-MU-α-Gal substrate (prepared in 50 mM sodium citrate/sodium phosphate buffer, pH 4.6) will be added to each well via a multi-channel pipettor. The plates will be sealed with cover tape and incubated at 37° C. for 1 hr. The enzymatic reactions will be halted by adding 125 µl of 0.1 M NaOH and the liberated 4-MU fluorescence will be read on a fluorescence plate reader using 355 nm excitation and 460 nm emission wavelengths, respectively. The 4-MU fluorescence from the mock-transfected sample will serve as the "background" control and will be subtracted from all GLA samples.

EXAMPLE 5

It was recognized that certain proteins are naturally expressed at very high levels while others are poorly expressed. While mRNA abundance and stability are important factors at the transcriptional level which can affect protein expression, it is becoming increasingly clear that signal sequences also play critical roles at the protein level and contribute to this disparate protein expression. Human immunoglobulin heavy chain binding protein (Bip) has specific characteristics that would be particularly advantageous for developing superior signal sequences to improve protein expression and secretion for recombinant proteins. One modified Bip signal sequence was made and appended to a model protein to determine if this unnatural signal sequence would improve protein expression and secretion for the model protein. Specifically, the hydrophobic core was lengthened to form a longer α-helix structure. It is predicted that the lengthening of the hydrophobic domain in modified Bip signal sequence-1 would have several advantages. First, the modified (longer) hydrophobic domain would form a longer α-helix and span the entire ribosomal exit tunnel that can be easily identified by the ribosomal protein Rpl17 to facilitate better interactions with other key ER proteins such as Sec61 subunits, and RAMP4. Second, a longer α-helical hydrophobic domain may enable this modified Bip signal sequence to interact with key translocon proteins such as TRAM and Sec61 subunits to help efficiently orient the nascent polypeptide at the translocon pore to promote the necessary protein translocation-competent loop orientation. Third, a longer α-helical hydrophobic domain may enable this modified Bip signal sequence to move out of the aqueous translocon pore and into the lipid bilayer more efficiently so that it can be cleaved by signal peptidase at a faster rate. Fourth, a modified Bip signal sequence may move away from the translocon at a faster rate to enable the recombinant protein to interact with other important proteins such as oligosaccharyltransferase, ER chaperone proteins such as Bip, protein disulfide isomerase and calnexin sooner during its synthesis to improve protein folding. Any or all of these potential benefits would improve the rate of protein expression, folding and export out of cells.

Other modifications can be made include adding charged residues to flanking regions of the extended hydrophobic domain to further enhance its hydrophobicity and to help properly orient the signal sequence at the translocon. These modifications are intended to enhance signal sequence interactions with certain ribosomal proteins, particularly Rpl17, which in turn would increase interactions with translocon proteins Sec61β, RAMP4 and TRAM to improve protein translocation, protein expression and secretion.

Several different DNA constructs encoding wild-type human GlcCerase were generated to contain either the native GlcCerase signal sequence (WT GlcCerase) or the human Bip signal sequence (CBP201 GlcCerase) or the novel modified Bip signal sequence-1 (CBP204 GlcCerase). These constructs (1 µg) were tested by transient expression experiments in human cell line (HEK293T) that were at ~80% confluency. Conditioned cell culture medium (20 µl) was harvested daily during a 72-hr time course and assayed for GlcCerase enzymatic activity using the 4-MU-β-glucose fluorogenic substrate to evaluate the effects of signal sequences on GlcCerase expression and secretion. As can be seen in FIG. 1, both signal sequences can promote the expression and secretion of GlcCerase into the cell culture medium. However, the engineered modified Bip signal sequence-1 (in CBP204 GlcCerase) was observed to yield 2-fold higher GlcCerase activity relative to WT GlcCerase 72 hrs post-transfection. Basal activity was seen for the mock-transfected (empty vector) negative control and confirmed that the increased enzyme activity resulted from expression of recombinant GlcCerase. Multiple transfection experiments (n>3) confirmed that the novel signal sequence increased GlcCerase expression and secretion.

EXAMPLE 6

Protein synthesis is highly affected by the availability of nutrients (i.e., ATP, amino acids, carbohydrates, etc.) as well as other essential cellular components (e.g., initiation and elongation factors, tRNAs, protein chaperones, etc.). The former can be increased or replenished with cell culture medium during re-feeding while the latter components are limited in cells and cannot be supplemented during protein production. Depletion of these vital components causes significant cellular stress which results in the reduction or even suspension of new protein synthesis for most proteins. Interestingly, the expression of some proteins is maintained and actually increased during these stressful periods as part of an adaptive cellular response to help cells return to homeostasis. It is not completely clear how these select proteins are distinguished by the cellular protein synthesis machinery to enable their preferential expression but signal sequences are believed to play an important role in this process. Since Bip is an important ER chaperone protein whose expression is maintained during this stressful period to help re-establish cellular homeostasis, we predict that this modified Bip signal sequence would enable preferential expression of the heterologous recombinant protein to be maintained under conditions where the expression of other proteins is reduced or suppressed. To test this hypothesis, we transfected KEK293T cell cultures at high cell density (~100% confluent) with WT GlcCerase and CBP204 GlcCerase and monitored their expression and secretion over a 63-hr period. Moreover, the cell culture medium was not changed during the experiment to deplete nutrients (during late stages of experiment to mimic periods of low nutrients during batch applications prior to re-feeding) to determine if the expression of WT GlcCerase and CBP204 GlcCerase changes in response to depletion of nutrients.

Figure 2:
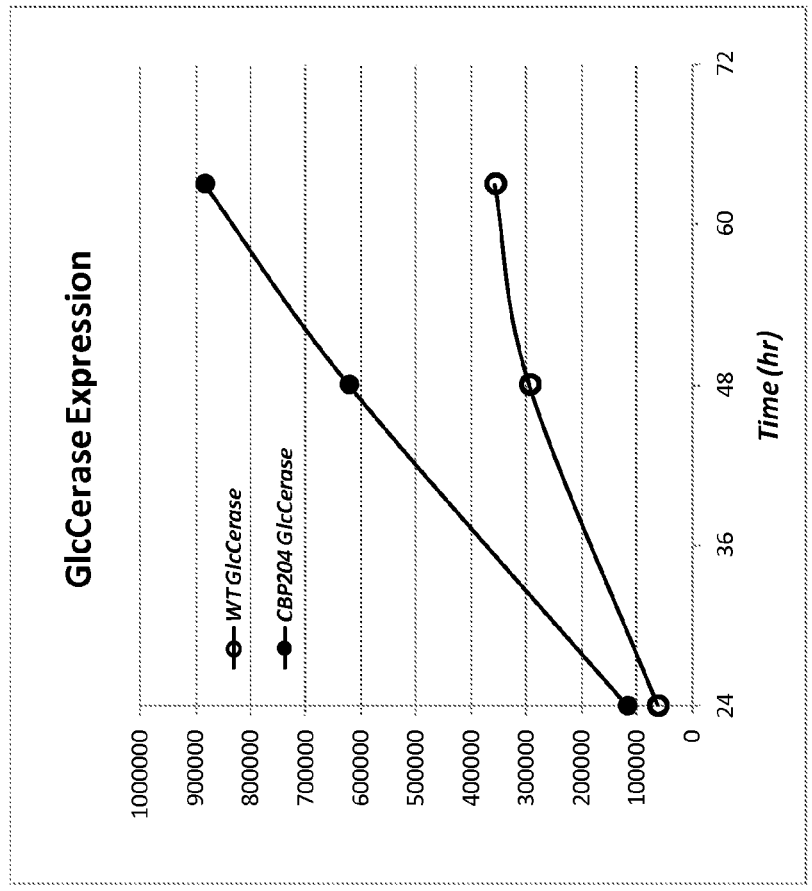
FIG. 2 shows the preferential expression and secretion of recombinant wild-type human acid β-glucocerebrosidase over a period of about 63 hours at high cell density and depleted nutrients.

Our results show that under these experimental conditions, CBP204 GlcCerase containing the modified Bip signal sequence-1 was expressed better than WT GlcCerase with its native signal sequence throughout the 63-hr period as shown in FIG. 2. CBP204 GlcCerase levels were 1.9-fold higher than WT GlcCerase after 24 hrs, 2.1-fold higher after 48 hrs and 2.5-fold higher after 63 hrs. When extrapolated to 72 hrs, CBP204 GlcCerase would be 3.3-fold higher than WT GlcCerase. Importantly, CBP204 GlcCerase expression was maintained at a near constant rate where there was a doubling of secreted protein after each day. In contrast, the expression rate for WT GlcCerase slowed significantly at the later time points. This difference was most evident when comparing the shape of the expression curves for these two enzymes—a near linear curve for CBP204 GlcCerase and a non-linear curve for WT GlcCerase as the rate of expression leveled off at the later time points. These data show differential expression of CBP204 GlcCerase and WT GlcCerase, presumably in response to nutrient depletion, and this divergence would be increased further with longer incubations. Since the only difference between CBP204 GlcCerase and WT GlcCerase is the signal sequence, these data support the hypothesis that the modified Bip signal sequence-1 enabled preferential expression during non-optimal cell culture conditions.

EXAMPLE 7

Figure 3:
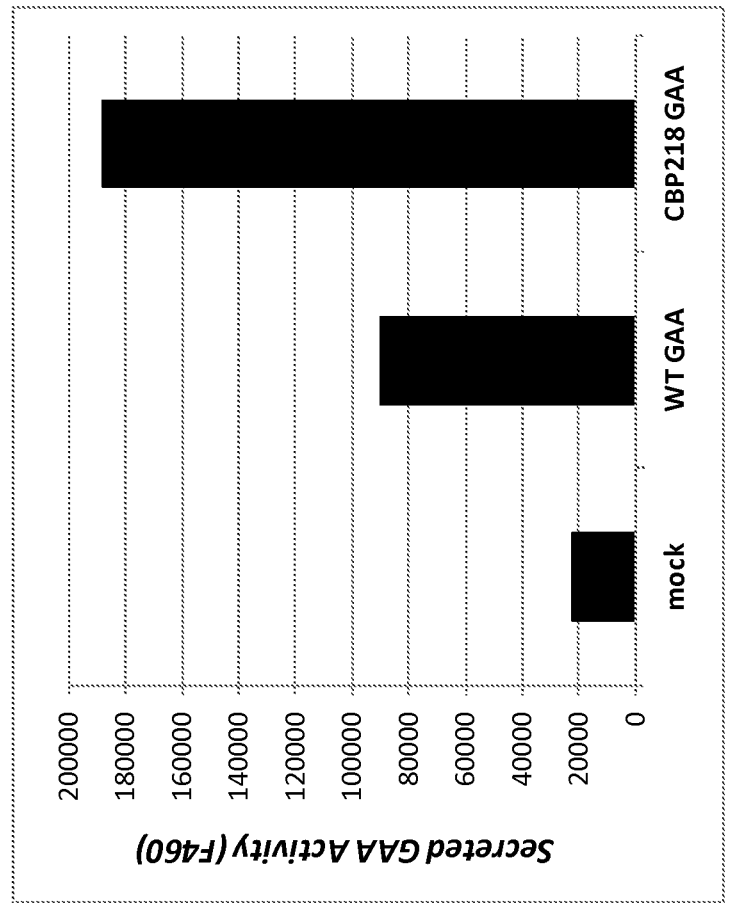
FIG. 3 shows the functional effect of signal sequences for the expression and secretion of recombinant wild-type human acid α-glucosidase over a period of about 43 hours.

To test the effects of the modified Bip signal sequence-1 on the expression and secretion of a different model protein, DNA plasmids were constructed to encode wildtype human acid α-glucosidase (GAA) containing either its native GAA signal sequence (WT GAA) or the engineered Bip signal sequence-1 and amino acid residues 24-952 of GAA (designated as CBP218 GAA). These DNA constructs were tested by transient expression in HEK293T over a ~2-day period to directly compare the effects of these signal sequences on the expression and secretion of wildtype GAA. As can be seen in FIG. 3, CBP218 GAA had a 2.5-fold higher secreted GAA activity in medium than WT GAA 43 hrs post-transfection. Basal activity was observed for the mock-transfected (empty vector) negative control and confirmed that the observed enzyme activity in medium resulted from expression of recombinant GAA. These results show that the modified Bip signal sequence-1 (in CBP218 GAA) significantly increased GAA expression and secretion under the same experimental conditions since only difference between CBP218 GAA and WT GAA is their respective signal sequences.

EXAMPLE 8

Western Blotting and ELISA Assays

The expression and secretion of test proteins will be evaluated by Western blot analysis. Briefly, conditioned cell culture medium from transient transfection experiments after 24, 48 or 72-hrs will be collected and subjected to sodium docecylsulfate polyacrylamide gel electrophoresis (SDS-PAGE) and subsequently transferred nitrocellulose membrane. The membrane will be blocked with 4% (w/v) non-fat milk in TRIS-buffered saline/0.1% (v/v) Tween-20 (TBST) for 1 hr at room temp with shaking. The membrane will then be incubated with the primary antibody (e.g., rabbit anti-human IGF-2) that had been appropriately diluted (e.g., 1:5000) in 4% (w/v) non-fat milk in TBST for 1 hr at room temp or overnight at 4° C. with shaking. The blot will then be washed with TBST at room temp with shaking and multiple buffer changes over 1 hr. The blot will then be incubated with an enzyme-linked secondary antibody (e.g., horseradish peroxidase-conjugated goat anti-rabbit antibodies) that had been appropriately diluted (e.g., 1:20,000) in 4% (w/v) non-fat milk in TBST for 1 hr at room temp with shaking. The blot will then be washed with TBST at room temp with shaking and multiple buffer changes over 1 hr. The blot will then be incubated with chemiluminescence substrate for 5 min at room temp and visualized by an imaging system or by film to assess the expression level of test protein.

Similarly, the expression of test proteins may be evaluated by enzyme-linked immunosorbent assays (ELISA). Briefly, 96-well immunosorbent plates will be coated with 50 μl of primary antibodies (e.g., rabbit anti-human IGF-2) at a protein concentration of 5 μg/ml in TRIS-buffered saline (TBS). These plates will then be blocked with 200 μl of 4% (w/v) non-fat milk in TBST for 1 hr at room temp. Conditioned cell culture medium from transient transfection experiments after 24, 48 or 72-hrs will be collected and incubated in these plates for 1 hr at room. These plates will then be washed with 200 μl TBST at room temp with shaking and multiple buffer changes over 1 hr. These plates will then be incubated with an enzyme-linked secondary antibody (e.g., horseradish peroxidase-conjugated goat anti-rabbit antibodies) that had been appropriately diluted (e.g., 1:20,000) in TBST for 1 hr at room temp. These plates will then be washed with TBST with multiple buffer changes over 1 hr at room temp. These plates will then be incubated with a colorimetric substrate (e.g., 3,3',5,5'-tetramethylbenzidine, TMB) for 5-15 min at room temp and stopped with 0.1 M sulfuric acid and read in a plate reader at the appropriate wavelength (e.g., 450 nm) to assess the expression of test protein.

What is claimed is:

1. A signal polypeptide comprising a modified fragment of human immunoglobulin heavy chain binding protein (Bip), wherein the modified fragment of human immunoglobulin heavy chain binding protein (Bip) has the amino acid sequence of SEQ ID NO: 19 with an insertion of seven to ten amino acid residues after position 13 of SEQ ID NO: 19, and wherein the last four inserted amino acid residues are leucine residues, and wherein the signal polypeptide is effective for a protein translocation when fused to the protein.

2. The signal polypeptide of claim 1 wherein the modified fragment of human immunoglobulin heavy chain binding protein (Bip) has the amino acid sequence of SEQ ID NO: 20.

3. The signal polypeptide of claim 1 wherein the modified fragment of human immunoglobulin heavy chain binding protein (Bip) has the amino acid sequence of SEQ ID NO: 21.

4. The signal polypeptide of claim 1 wherein the modified fragment of human immunoglobulin heavy chain binding protein (Bip) has the amino acid sequence of SEQ ID NO: 22.

5. The signal polypeptide of claim 1 wherein the modified fragment of human immunoglobulin heavy chain binding protein (Bip) has the amino acid sequence of SEQ ID NO: 23.

6. A fusion protein comprising the signal polypeptide of claim 1 operably linked to a heterologous polypeptide.

7. The fusion protein of claim 6 wherein the modified fragment of human immunoglobulin heavy chain binding protein (Bip) polypeptide signal sequence has amino acid sequence of SEQ ID NO: 20.

8. The fusion protein of claim 6 wherein the modified fragment of human immunoglobulin heavy chain binding protein (Bip) polypeptide signal sequence has the amino acid sequence of SEQ ID NO: 21.

9. The fusion protein of claim 6 wherein the modified fragment of human immunoglobulin heavy chain binding protein (Bip) polypeptide signal sequence has the amino acid sequence of SEQ ID NO: 22.

10. The fusion protein of claim 6 wherein the modified fragment of human immunoglobulin heavy chain binding protein (Bip) polypeptide signal sequence has the amino acid sequence of SEQ ID NO: 23.

11. The fusion protein of claim 6 wherein the heterologous polypeptide comprises one or more enzymes, one or more biological response modifiers, one or more toxins, one or more antibodies, one or more fragments of the heterologous polypeptide, or any combination thereof.

12. The fusion protein of claim 6 wherein the modified fragment of human immunoglobulin heavy chain binding protein (Bip) polypeptide signal sequence has the amino acid sequence of SEQ ID NO: 20 and the heterologous polypeptide comprises one or more of the following: acid β-glucocerebrosidase, acid α-galactosidase, acid α-glucosidase, proinsulin, insulin-like growth hormone-2 (IGF-2), interferon, therapeutic antibody and an insulin-like growth hormone-1 (IGF-1).

13. The fusion protein of claim 6 wherein the modified fragment of human immunoglobulin heavy chain binding protein (Bip) polypeptide signal sequence has the amino acid sequence of SEQ ID NO: 21 and the heterologous polypeptide comprises one or more of the following: acid β-glucocerebrosidase, acid α-galactosidase, acid α-glucosidase, proinsulin, insulin-like growth hormone-2 (IGF-2), interferon, therapeutic antibody or an insulin-like growth hormone-1 (IGF-1).

14. The fusion protein of claim 6 wherein the modified fragment of human immunoglobulin heavy chain binding protein (Bip) polypeptide signal sequence has the amino acid sequence of SEQ ID NO: 22 and the heterologous polypeptide comprises one or more of the following: acid β-glucocerebrosidase, acid α-galactosidase, acid α-glucosidase, proinsulin, insulin-like growth hormone-2 (IGF-2), interferon, therapeutic antibody or an insulin-like growth hormone-1 (IGF-1).

15. The fusion protein of claim 6 wherein the modified fragment of human immunoglobulin heavy chain binding protein (Bip) polypeptide signal sequence has the amino acid sequence of SEQ ID NO: 23 and the heterologous polypeptide comprises one or more of the following: acid β-glucocerebrosidase, acid α-galactosidase, acid α-glucosidase, proinsulin, insulin-like growth hormone-2 (IGF-2), interferon, therapeutic antibody or an insulin-like growth hormone-1 (IGF-1).

16. A method of producing a polypeptide, comprising:
  (a) expressing a fusion protein comprising the signal polypeptide of claim 1 operably linked to a heterologous polypeptide; and
  (b) recovering said heterologous polypeptide.

17. A method of increasing protein expression, comprising:
  (a) expressing a fusion protein comprising the signal polypeptide of claim 1 and a heterologous protein, and
  (b) recovering the heterologous protein.

18. A method of increasing protein secretion, comprising:
(a) expressing a fusion protein comprising the signal polypeptide of claim 1 and a heterologous protein, and
(b) recovering the heterologous protein.

* * * * *